(12) United States Patent
Roman

(10) Patent No.: US 6,245,571 B1
(45) Date of Patent: Jun. 12, 2001

(54) METHOD OF CHARACTERIZING THE NEUTRALIZATION CAPACITY OF A LUBRICANT AND DEVICE FOR THE IMPLEMENTATION OF THIS METHOD

(75) Inventor: Jean-Philippe Roman, Lyons (FR)

(73) Assignee: Elf Antar France, Courbevoie (FR)

( * ) Notice: Subject to any disclaimer, the term of this patent is extended or adjusted under 35 U.S.C. 154(b) by 0 days.

(21) Appl. No.: 09/225,311

(22) Filed: Jan. 5, 1999

(30) Foreign Application Priority Data

Jan. 16, 1998 (FR) .................................................. 98 00457

(51) Int. Cl.[7] .................................................. G01N 33/22
(52) U.S. Cl. .................................. 436/61; 436/6; 436/60; 436/102; 436/148; 73/10; 73/53.05; 73/53.06; 422/53; 422/68.1
(58) Field of Search ................................ 436/60, 61, 148, 436/163; 425/223, 224; 73/53.05; 264/165

(56) References Cited

U.S. PATENT DOCUMENTS

| 3,671,430 | * | 6/1972 | Corringer ........................... 252/32.7 |
| 5,366,898 | * | 11/1994 | Hangstrom et al. .................... 436/60 |

FOREIGN PATENT DOCUMENTS

| 254705 | * | 1/1988 | (CS) . |
| 217 895 | | 1/1985 | (DD) .............................. C10M/1/40 |
| 3625741 | * | 2/1987 | (DE) . |
| 2 141 414 | | 1/1973 | (FR) ................................. C01N/7/00 |
| 2 486 246 | | 1/1982 | (FR) .............................. G01N/21/35 |

OTHER PUBLICATIONS

Akiyama et al. "Cylinder wear mechanism in an EGR–equipped diesel engine and wear protection by the engine oil", SAE Technical Paper Series, # 872158, pp. 4–11, 1987.*
Patent Abstracts of Japan, vol. 13, No. 175 (P–863), Apr. 25, 1989 & JP 01 009 364 A (Tatsuta Electric Wire & Cable Co. Ltd.) Jan. 21, 1989.

* cited by examiner

Primary Examiner—Jill Warden
Assistant Examiner—Yelena Gakh
(74) Attorney, Agent, or Firm—Blank Rome Comisky & McCauley LLP

(57) ABSTRACT

The invention relates to the study and the manufacture of lubricants used in particular in diesel engines. According to the invention, the neutralization capacity of a lubricant comprising detergent additives is determined by a method which consists in reacting, in a leaktight tank, at a constant temperature, the bases contributed by the additives present in a lubricant film of known mass with a predetermined amount of a liquid acid and in recording, as a function of the time, the values of the pressure within the leaktight tank, and in then determining, from the recorded values of the pressure, at lest one of the following three characterizing parameters: an initiation period for the reaction, a neutralization potential and a reaction rate. The invention finds its application in research and control laboratories of manufacturers of lubricants and in those of engine manufacturers.

18 Claims, 4 Drawing Sheets

METHOD OF CHARACTERIZING THE NEUTRALIZATION CAPACITY OF A LUBRICANT AND DEVICE FOR THE IMPLEMENTATION OF THIS METHOD

TECHNICAL FIELD

The present invention relates to a method of characterizing the neutralization capacity of a lubricant comprising detergent additives including a reserve stock of basicity and to a device for the implementation of this method.

It finds its application in research and control laboratories of manufacturers of lubricants and in those of engine manufacturers.

STATE OF THE PRIOR ART

Diesel engines and more particularly large-size marine diesel engines generally use heavy fuel oils with a high sulphur content as fuels. During combustion, the sulphur can result in the formation of sulphuric acid under the effect of oxidation reactions or by combination with water.

This acid, which has a tendency to condense within the diesel engines, can result in corrosion of the metal parts and corrosive wear of major components, such as linings and sections.

In order to minimize these harmful effects, the lubricants used for these engines must exhibit a neutralization capacity.

For this reason, these lubricants are products of high basicity.

This basicity is usually contributed by overbased detergent additives which include a neutralizing species, for example calcium carbonate.

Use is commonly made, in measuring this basicity, of a method described in ASTM Standard D-2896, which makes it possible to determine a parameter, known as BN (Basic Number), which is expressed as mg of potassium hydroxide (KOH) per gram of lubricant.

This parameter is a macroscopic indicator which makes it possible to classify lubricants according to the potential necessary in order to ensure satisfactory and lasting protection of engines with respect to undesirable phenomena related to the presence of acids in general.

This parameter, representative of the basicity of the lubricant, does not take into account the true conditions of oxidation of the lubricants in diesel engines; it therefore cannot fully characterize their neutralization capacity.

Another method of characterizing the neutralization capacity of lubricants is described in the document Technical Papers Series, No. 872,158, entitled "Cylinder Wear Mechanism in an EGR-Equipped Diesel Engine and Wear Protection by the Engine Oil", published by the Society of Automotive Engineers.

This method is targeted at measuring the rate of neutralization of the lubricant by sulphuric acid. It consists in introducing a 30 gram sample of lubricant into a leaktight tank equipped with a thermometer and a manometer and including a vent.

The tank being immersed in a water bath at a constant temperature and the lubricant sample being continually stirred by suitable means, 0.1 milliliter of concentrated sulphuric acid is introduced within the tank, when the temperature of the sample has stabilized, by means for a syringe through the open vent.

The vent is then immediately closed.

Starting at this moment, the pressure indicated by the manometer is recorded for 10 minutes.

The values of the recorded pressure are converted into the amount of carbon dioxide produced by the reaction of the sulphuric acid with the basic products present in the lubricant sample.

The rate of neutralization is characterized by the volume of carbon dioxide produced during the 4 minutes which follow the introduction of the acid; it is expressed as micromoles of carbon dioxide.

This method exhibits the disadvantage of employing a large volume of lubricant, whereas, on the other hand, in an operating engine, the neutralization phenomena occur at the surface of the lubricated components, such as the cylinders and pistons, and the amounts of lubricants involved are low.

With this method, the measurement of the rate of neutralization is very dependent on the stirring conditions of the lubricant in the tank inside which the reaction is carried out, which is unfavourable to the repeatability of the measurement and to the validity of the comparisons between measurements carried out with different lubricants.

Furthermore, it is representative only of slow phenomena, that is to say lasting several minutes.

ACCOUNT OF THE INVENTION

The object of the present invention is specifically to overcome these disadvantages and in particular to provide a process and a device for characterizing the neutralization capacity of lubricants which takes into account the true conditions of oxidation of lubricants in engines. This is because the results obtained by the method of the invention are representative of the neutralization phenomena which take place essentially at the surface of the lubricated components, which are characterized by low amounts of lubricants involved at any instant and high local concentrations of acid, which result from the phenomena of condensation and of solubilization of the acid in the lubricant.

It finds it application in the laboratories of the industries in which lubricants are manufactured and those of the constructors of engines for which these lubricants are intended.

To this end, the present invention provides a method of characterizing the neutralization capacity of a lubricant comprising detergent additives including a reserve stock of basicity, which consists in reacting, in a leaktight tank, at a constant temperature, the bases contributed by the additives present in a sample of known mass of lubricant with a predetermined amount of liquid acid at least equal to the stoichiometric amount, characterized in that it additionally consists:

in forming, within the leaktight tank, a film from the lubricant sample,
in depositing the predetermined amount of liquid acid at the surface of the film in a time of less than 0.5 second,
in recording, as a function of the time, the values of the pressure within the leaktight tank until the said pressure has stabilized;
in determining, from the recorded values of the pressure, at least one of the following three characterizing parameters: an initiation period for the reaction, a neutralization potential and a reaction rate.

According to a second characteristic of the method of the invention, the initiation period for the reaction is determined by the measurement of the time which passes between the beginning of the deposition of the liquid acid and the moment of passing through a minimum value of the recorded pressure.

According to another characteristic of the method of the invention, the amount of bases contributed by the detergent additives present in the lubricant sample being known and the recorded pressure reaching a stable value, the neutralization potential is determined by application of the following formula:

$$Ra = \frac{\Delta P}{Pth} \times 100$$

in which:

Ra represents the neutralization potential in %,

ΔP represents the difference between the stabilized recorded pressure value and the minimum value of the recorded pressure, Pth represents the theoretical pressure in the leaktight tank which would have been reached if the reaction had been complete.

According to another characteristic of the method, the reaction rate is equal to the maximum rate of increase in the recorded pressure.

According to another characteristic of the method of the invention, the lubricant film formed within the leaktight tank exhibits a thickness of between 20 and 150 microns.

According to another characteristic of the method of the invention, the liquid acid is preferably 95% sulphuric acid.

According to another characteristic of the method of the invention, the predetermined amount of 95% sulphuric acid corresponds to an excess of acid of between 0.5% and 200% and preferably equal to 96.7% with respect to the amount of bases contributed by the detergent additives.

Another subject-matter of the invention is a device for the characterization of the neutralization capacity of a lubricant comprising detergent additives including a reserve stock of basicity, comprising a leaktight tank equipped with means for maintaining at a constant temperature, in which the bases contributed by the additives present in a sample of known mass of lubricant are reacted with a predetermined amount of liquid acid at least equal to the stoichiometric amount, characterized in that it additionally comprises:

means for forming a film on an inner wall of the leaktight tank from the lubricant sample, means for depositing the predetermined amount of liquid acid at the surface of the film in a time of less than 0.5 second, a pressure-measuring sensor within the leaktight tank delivering a pressure measurement signal to an output, a recording unit connected to the output of the pressure sensor, in order to record, as a function of the time, the values of the pressure within the leaktight tank, means for determining at least one of the following three characterizing parameters: an initiation period for the reaction, a neutralization potential or a reaction rate.

According to another characteristic of the device of the invention, the means for determining the characterizing parameters consist of a unit for displaying a curve representative of the value of the recorded pressure as a function of the time in a system of graduated axes, the said unit being connected to an output of the recording unit.

According to another characteristic of the device of the invention, the initiation period for the reaction is determined from the curve representative of the value of the recorded pressure by the measurement of the time which passes between the beginning of the deposition of the liquid acid and the moment of passing through a minimum value of the recorded pressure.

According to another characteristic of the device of the invention, the amount of bases contributed by the detergent additives present in the lubricant sample being known and the recorded pressure reaching a stable value, the neutralization potential is determined by application of the following formula:

$$Ra = \frac{\Delta P}{Pth} \times 100$$

in which:

Ra represents the neutralization potential in %,

ΔP represents the difference between the stabilized recorded pressure value and the minimum value of the recorded pressure, Pth represents the theoretical pressure in the leaktight tank which would have been reached if the reaction had been complete, ΔP is determined from the curve representative of the value of the recorded pressure.

According to another characteristic of the device of the invention, the reaction rate, equal to the maximum rate of increase in the recorded pressure, is determined from the curve representative of the value of the recorded pressure.

According to another characteristic, the device of the invention additionally comprises an indicator of the beginning of the deposition of liquid acid which delivers a signal for the beginning of deposition of liquid acid to an output connected to the recording unit and the means for determining the characterizing parameters consist of an electronic unit for calculating the said parameters connected to an output of the recording unit.

According to another characteristic of the device of the invention, the electronic calculating unit determines the initiation period for the reaction, from the value of the recorded pressure and the signal delivered by the indicator of the beginning of the deposition of liquid acid, by calculating the time which passes between the beginning of the deposition of the liquid acid and the moment of passing through a minimum value of the recorded pressure.

According to another characteristic of the device of the invention, the amount of bases contributed by the detergent additives present in the lubricant sample being known and the recorded pressure reaching a stable value, the neutralization potential is determined by application of the following formula:

$$Ra = \frac{\Delta P}{Pth} \times 100$$

in which:

Ra represents the neutralization potential in %,

ΔP represents the difference between the stabilized recorded pressure value and the minimum value of the recorded pressure, Pth represents the theoretical pressure in the leaktight tank which would have been reached if the reaction had been complete, ΔP is calculated by the electronic calculating unit from the values of the recorded pressure.

According to a final characteristic of the device of the invention, the electronic calculating unit determines the reaction rate from the values of the recorded pressure by calculating the maximum rate of increase in the recorded pressure.

BRIEF DESCRIPTION OF THE DRAWINGS

The invention will be better understood with the help of the following description of two embodiments given by way of examples and with reference to the appended drawings, in which.

DETAILED ACCOUNT OF THE INVENTION

Generally, the method and the device of the invention are used to characterize the neutralization capacity of a lubricant comprising detergent additives including a reserve stock of basicity.

Figure 1:
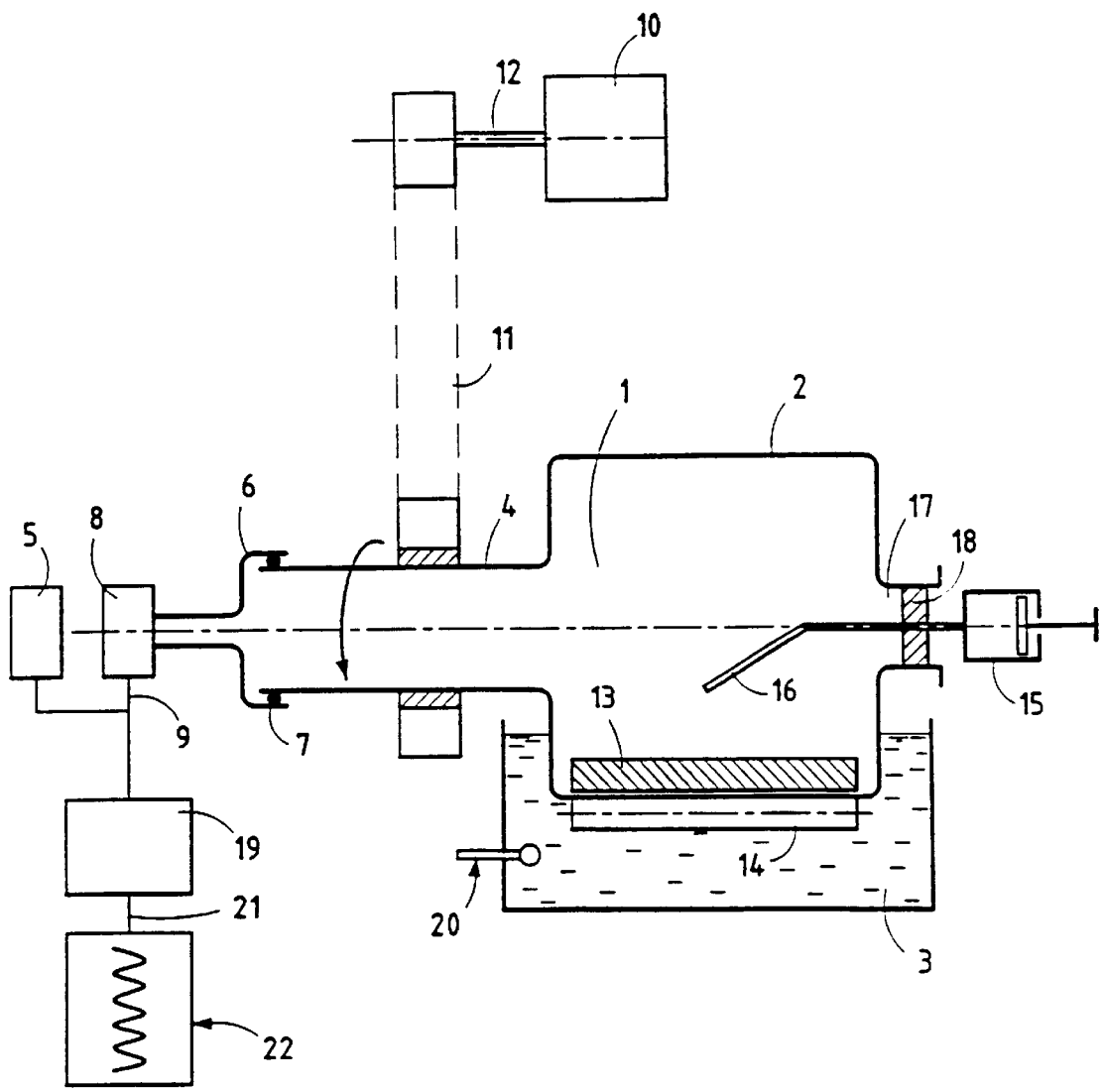
FIG. 1 diagrammatically represents a first embodiment of the device of the invention comprising a plotter.

FIG. 1 diagrammatically represents a first embodiment of the device of the invention for determining the parameters which characterize the neutralization capacity of lubricants from measurement results displayed on a graphic output unit.

The device according to this first embodiment comprises:
- a transparent leaktight tank 1 of cylindrical shape with a horizontal axis composed of a body 2 extended by a neck 4 with a smaller diameter closed by an end cap 6, the leaktightness between the neck 4 and the end cap 6 being provided by an O-ring seal 7,
- a rapid-response pressure sensor 8 fitted in a leaktight way to the end cap 6, which delivers a signal representative of the pressure within the leaktight tank 1 to an output 9,
- a pressure indicator 5 connected to the output 9 of the pressure sensor 8,
- a fast recorder 19 connected electrically to the output 9 of the pressure sensor 8,
- a curve plotter 22 connected to an output 21 of the recorder 19,
- an electric motor 10 equipped with an axis 12 which drives in rotation about its horizontal axis the body 2 of the tank 1 by virtue of the connecting means 11,
- a thermostatically-controlled bath 3 in which the lower part of the body 2 of the tank 1 is partially immersed, the temperature of which is measured by a thermometer 20 and regulated by suitable means not represented in FIG. 1,
- a syringe 15 equipped with a needle 16 with a curved shape at its free end.

Figure 2:
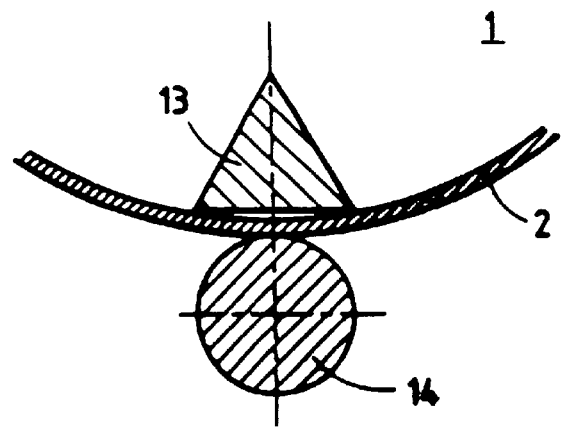
FIG. 2 is a partial cross-sectional view which shows the respective positions of the body of the leaktight tank and of the magnetic bars of the device of the invention.

In addition, the device of the invention comprises, placed within the body 2, a first cylindrical magnetic bar 13, the cross-section of which has the shape of an equilateral triangle, with a height substantially equal to 0.08 times the diameter of the body 2 and with a length slightly less than the length of a generator of the body 2, and, placed outside the body 2, a second cylindrical magnetic bar 14, of circular cross-section, with a diameter comparable to the height of the first magnetic bar, these two magnetic bars 13 and 14 being positioned facing one another at the bottom part of he body 2, so that they are mutually attracted under the effect of their magnetic field. The detail of the relative positions of the body 2 and of the magnetic bars 13 and 14 is represented in FIG. 2.

The body 2 of the leaktight tank 1 comprises, on the face opposite the neck 4, an axial opening 17 closed by a septum 18.

The value at which it is desired to operate, for example 80° C., is fixed by acting on the means for regulating the temperature of the thermostatically-controlled bath 3. When this temperature, measured by the thermometer 20, is reached and stabilized, the septum 18 is removed and a predetermined amount of the lubricant for which it is desired to characterize the neutralization capacity is introduced via the opening 17 within the body 2 of the tank 1 and then the septum 18 is reinstated.

The predetermined amount of lubricant is calculated from the dimensions of the body 2 of the tank and from the thickness of the film which it is desired to form.

The electric motor 10 which rotates the tank 1 via the driving means 11 which connect the axis 12 of the motor to the tank 1 is powered. The rotational speed of the tank is, for example, 1.5 revolutions per second.

The magnetic bars 13 and 14 interact with the wall of the lower part of the tank 1 to form a film of lubricant with a thickness of between 20 and 150 microns. After rotating the tank 1 for a few minutes, it is confirmed visually that the film formed is homogeneous; its temperature is then very close to that of the thermostatically-controlled bath.

This state is reached when the pressure within the tank 1, indicated by the pressure indicator 5, no longer varies.

The needle 16 of the syringe 15, filled beforehand with a liquid acid, is then introduced manually within the tank 1 through the septum 18, so that its curved free end is directed towards the lower part of the body 2 of the tank 1 immersed in the thermostatically-controlled bath 3. An amount of sulphuric acid at least equal to the stoichiometric amount for reacting with the basic components contributed by the additives present in the lubricant film is expelled in a time of the order of 0.5 second by acting manually on the piston of the syringe 15. To facilitate this operation, the motor 10 can be halted for a very brief instant. This amount of acid thus introduced into the tank 1 is deposited on the lubricant film, with which it reacts.

The acid/base reaction releases carbon dioxide, the effect of which is to increase the pressure in the leaktight tank 1.

Simultaneously with the beginning of the deposition of acid, the recording of the pressure within the tank 1 is started. This recording is continued until the pressure no longer varies, that is to say for approximately 10 seconds.

Figure 3:
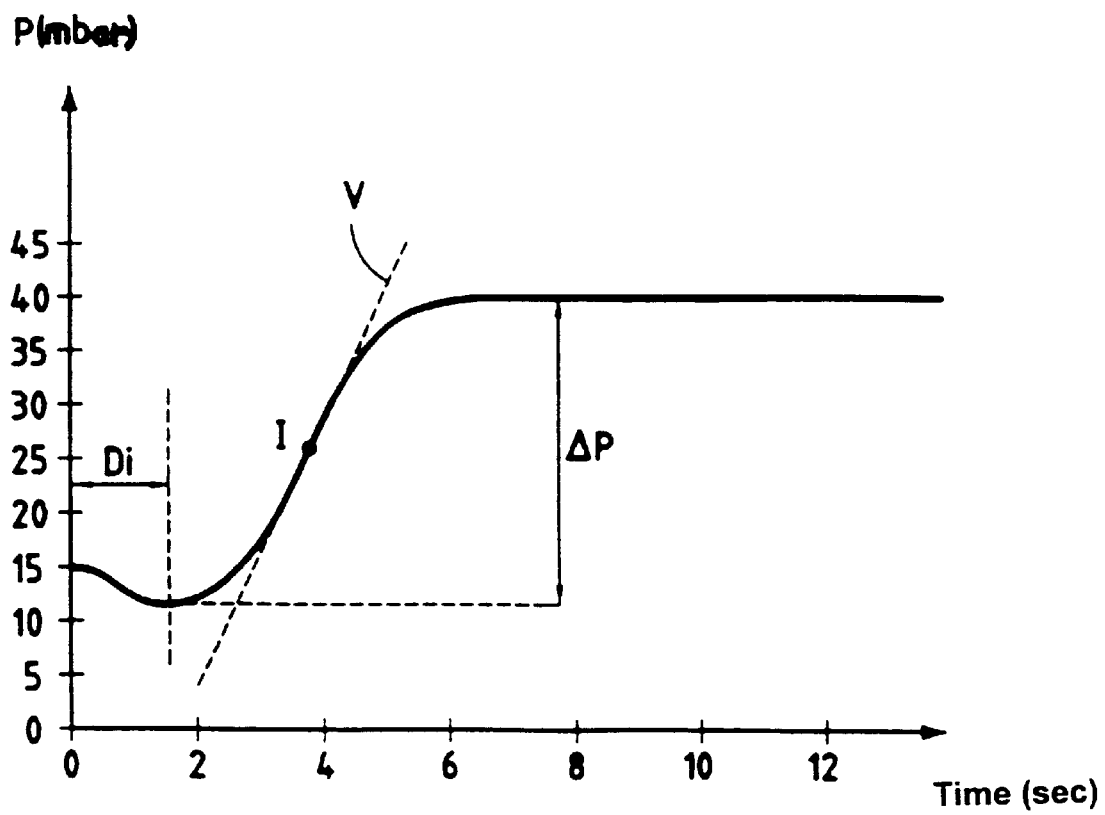
FIG. 3 represents a curve of variation in the pressure within the tank of the device of the invention as a function of the time, FIG. 4 diagrammatically represents a second embodiment of the device of the invention which comprises an electronic calculating unit.

The curve of variation in the pressure as a function of the time is thus obtained on the plotter 22, an example of which is given in FIG. 3.

Three regions can be distinguished on this curve corresponding to the three phases of the reaction: the initiation phase, which corresponds to the solubilization of the acid and to its diffusion, the reaction phase proper and the phase of halting or limiting the reaction.

The three parameters characterizing:
- the initiation period for the reaction, given by the measurement of the time which passes between the beginning of the introduction of the acid into the tank 1 and the moment at which the pressure reaches its minimum value. It corresponds to the time interval indicated by Di in FIG. 3.

the neutralization potential

It is observed that the pressure within the tank stabilizes at a value lower than the theoretical pressure which would have been reached if all the base available in the film had reacted, which can be calculated by means for the known formula given below. The acid/base reaction is therefore incomplete. This result is entirely surprising since, the acid introduced into the tank being in excess, all the bases present in the film ought to have reacted.

The neutralization potential is defined by the following formula:

$$Ra = \frac{\Delta P}{Pth} \times 100$$

in which:

Ra represents the neutralization potential in %, $\Delta P$ is equal to the difference between the stabilized recorded pressure value and the minimum value of the recorded pressure, indicated by $\Delta P$ in FIG. 3, Pth represents the theoretical pressure of the carbon dioxide in the leaktight tank which would have been reached if the reaction had been complete.

Pth is calculated from the following known formula:

$$Pth=Nth.R.T/V$$

in which

Pth is expressed in pascals,

Nth is the theoretical number of moles of carbon dioxide which would have been produced if the reaction had been complete, R is the ideal gas constant, equal to 8.32 $J.K^{-1}.mol^{-1}$, V represents the volume of the tank, expressed in cubic meters T represents the temperature of the thermostatically-controlled bath, expressed in kelvins.

Nth is calculated from the BN (Basic Number) of the lubricant, determined beforehand according to the method described in ASTM Standard D 2896, from the mass of the lubricant introduced into the tank in order to form the film and from the acid used. BN is expressed as mg of potassium hydroxide per gram of lubricant.

The reaction rate

It is equal to the maximum rate of variation in the recorded pressure. It corresponds to the slope of the curve in FIG. 3 calculated at the inflexion point indicated by I. It is characteristic of first order kinetics and represents physically the phenomenon of neutralization of the lubricant in the form of a thin film are determined from this curve.

One of the main advantages of the method of the invention is that it takes into account separately the rapid phenomena which take place in the seconds which follow the introduction of acid into the leaktight tank.

The three parameters, thus determined under conditions close to those under which a lubricant has to be used, characterize in a precise way its neutralization capacity.

EXAMPLE

Main Characteristics of the Leaktight Tank nature: transparent glass diameter of the body 2: 100 mm length of the body 2: 65 mm diameter of the neck: 40 mm total volume V: $7.5 \times 10^{-4} m^3$ Characteristics of the Magnetic Bars height of the first bar 13: 11 mm height of the second bar 14: 11 mm Pressure Sensor type: ELESTA CP 1100 sensitivity: 0.02 mbar scale: 0 to 100 mbar response time: 100 ms

Recorder graphic output unit:

sensitivity: 50 ms run speed: 0.25 cm/s

Rotational Speed of the Tank 1.5 revolutions per second

Temperature of the Thermostatically-controlled Bath

80° C., i.e. 353 K

Data Relating to the Lubricant type: for marine engine

BN according to ASTM Standard D 2896: 70 mg KOH/g of lubricant amount introduced into the tank in order to form the film: 2 g neutralizing species: calcium carbonate ($CaCO_3$)

Data Relating to the Liquid Acid nature: 95% sulphuric acid amount deposited on the film: 2 ml excess calculated with respect to the stoichiometry: 96.7%

Calculation of the Pth Value

Pth=Nth.R.T/V

Figure 5:
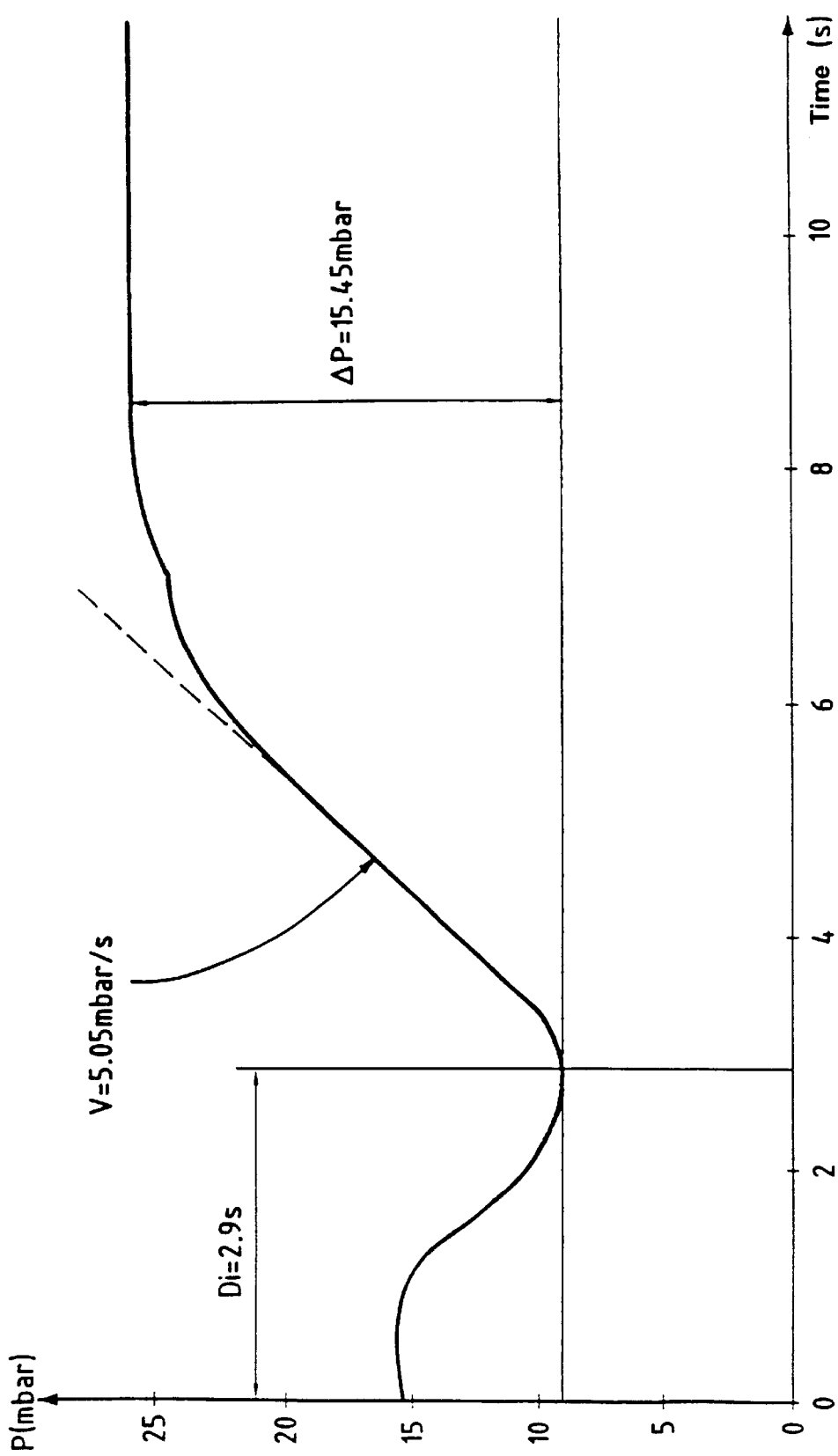
FIG. 5 represents the curve of variation in the pressure within the tank of the device of the invention as a function of the time obtained with a lubricant exhibiting a BN of 70 mg KOH/g.

Number of moles of KOH in the lubricant:

mass of KOH/KOH molar mass mass of lubricant×BN/KOH molar mass, i.e. $2 \times 70 \times 10^{-3}/56 = 0.0025$ mol of KOH, from which Nth= 0.0025/2=0.00125 mol of $CaCO_3$ R=8.32 $J.K^{-1}.mol^{-1}$, T=273+80=353 K, V=$7.5 \times 10^{-4} m^3$ Pth=$1.25 \times 10^{-3} \times 8.32 \times 353 / 7.5 \times 10^{-4}$=4895 Pa, i.e. 48.95 mbar The curve obtained is that in FIG. 5, from which are determined the parameters characterizing the neutralization capacity of the lubricant indicated below:

initiation period (measured on FIG. 5): 2.9 seconds neutralization potential: from the $\Delta P$ value measured on FIG. 5, i.e. 15.4 mbar, and the Pth value, Ra is calculated by application of the formula Ra=($\Delta P$/Pth)× 100, i.e. Ra=(15.4/48.9)×100=31.6% reaction rate (measured on FIG. 5): 5.05 mbar/second

Figure 4:
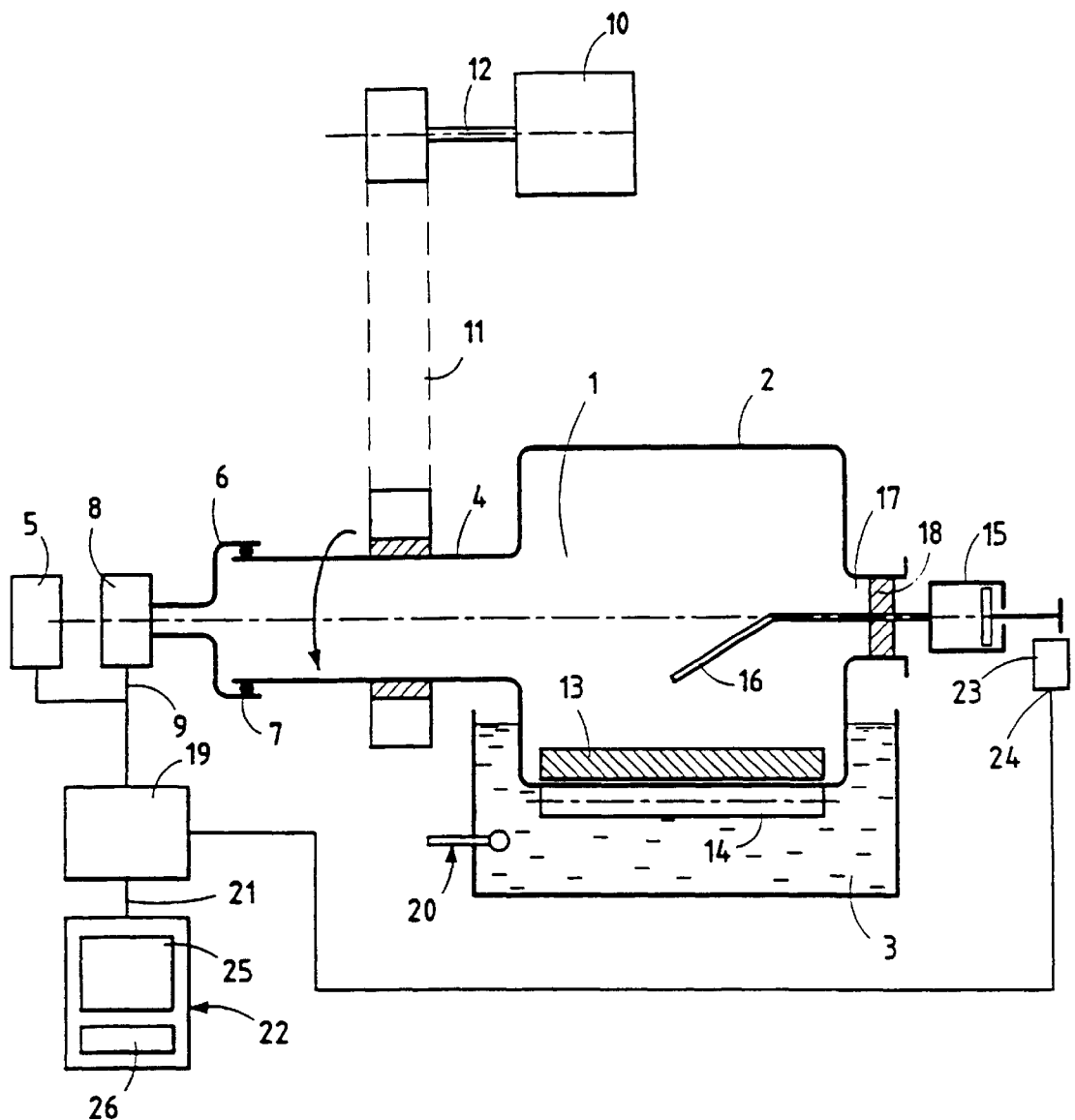

According to a second embodiment represented diagrammatically in FIG. 4, the device of the invention comprises:

a transparent leaktight tank 1 of cylindrical shape with a horizontal axis composed of a body 2 extended by a neck 4 with a smaller diameter closed by an end cap 6, the leaktightness between the neck 4 and the end cap 6 being provided by an O-ring seal 7, a rapid-response pressure sensor 8 fitted in a leaktight way to the end cap 6, which delivers a signal representative of the pressure within the leaktight tank 1 to an output 9, a pressure indicator 5 connected to the output 9 of the pressure sensor 8, a microcontact 23 indicating the beginning of the deposition of acid, a recorder 19 connected electrically to the output 9 of the pressure sensor 8 and to an output 24 of the indicator 23 of the beginning of the deposition of acid, an electronic calculating unit 25 connected to an output 21 of the recorder 19 comprising: a liquid-crystal numerical indicator 26 and, not represented in FIG. 4, a processing unit, a memory and a numeric keypad for introducing data into the memory, an electric motor 10 equipped with an axis 12 which drives in rotation about its horizontal axis the body 2 of the tank 1 by virtue of the connecting means 11, a thermostatically-controlled bath 3 in which the lower part of the body 2 of the tank 1 is partially immersed, the temperature of which is measured by a thermometer 20 and regulated by suitable means not represented in FIG. 4.

In addition, the device of the invention comprises, placed within the body 2, a first cylindrical magnetic bar 13, the cross-section of which has the shape of an equilateral triangle, with a height substantially equal to 0.08 times the diameter of the body 2 and with a length slightly less than the length of a generator of the body 2, and, placed outside the body 2, a second cylindrical magnetic bar 14, of circular cross-section, with a diameter comparable to the height of the first magnetic bar, these two magnetic bars 13 and 14 being positioned facing one another at the bottom part of the body 2, so that they are mutually attracted under the effect of their magnetic field. The detail of the relative positions of the body 2 and of the magnetic bars 13 and 14 is represented in FIG. 2.

The body 2 of the leaktight tank 1 comprises, on the face opposite the neck 4, an axial opening 17 closed by a septum 18, a needle 16 of a syringe 15 passing through this septum. This needle 16, which is curved in shape, has its free end directed towards the bottom part of the body 2 immersed in the thermostatically-controlled bath.

The value at which it is desired to operate, for example 80° C., is fixed by acting on the means for regulating the temperature of the thermostatically-controlled bath 3. When this temperature, measured by the thermometer 20, is reached and stabilized, the septum 18 is removed and a predetermined amount of the lubricant for which it is desired to characterize the neutralization capacity is introduced via the opening 17 within the body 2 of the tank 1 and then the septum 18 is reinstated.

The predetermined amount of lubricant is calculated from the dimensions of the body 2 of the tank and from the thickness of the film which it is desired to form.

The electric motor 10 which rotates the tank 1 via the driving means 11 which connect the axis 12 of the motor to the tank 1 is powered. The rotational speed of the tank is, for example, 1.5 revolutions per second.

The magnetic bars 13 and 14 interact with the wall of the lower part of the tank 1 to form a film of lubricant with a thickness of between 20 and 150 microns. After lubricating for a few minutes, it is confirmed visually that the film formed is homogeneous; its temperature is then very close to that of the thermostatically-controlled bath.

This state is reached when the pressure within the tank 1, indicated by the pressure indicator 5, no longer varies.

The needle 16 of the syringe 15, filled beforehand with a liquid acid, is then introduced manually within the tank 1 through the septum. An amount of sulphuric acid at least equal to the stoichiometric amount for reacting with the basic components contributed by the additives present in the lubricant film is expelled in a time of the order of 0.5 second by acting either manually or via a microactuator on the piston of the syringe 15. To facilitate this operation, the motor 10 can be halted for a very brief instant. This amount of acid thus introduced into the tank 1 is deposited on the lubricant film, with which it reacts.

At the moment of the beginning of the action on the piston of the syringe 15, the microcontact 23 is actuated and delivers an electrical signal to its output 24 connected to an input of the recorder 19.

The acid/base reaction releases carbon dioxide, the effect of which is to increase the pressure in the leaktight tank 1.

At the moment of appearance of the signal delivered by the microcontact, the recorder 19 begins to record the pressure within the tank 1. This recording takes place automatically for a period at least equal to 60 seconds.

The values of the pressure which are recorded by the recorder 19 are transmitted to the electronic calculating unit 25.

From these values, the electronic unit 25 executes a program stored in its memory in order to calculate the three characterizing parameters:

the initiation period for the reaction, given by the measurement of the time which passes between the moment of appearance of the signal delivered by the indicator 23 of the beginning of the introduction of the acid into the tank 1 and the moment at which the pressure reaches its minimum value.

the neutralization potential, defined by the following formula:

$$Ra = \frac{\Delta P}{Pth} \times 100$$

in which:

Ra represents the neutralization potential in %, $\Delta P$ is equal to the difference between the stabilized recorded pressure value and the minimum value of the recorded pressure, Pth represents the theoretical pressure of the carbon dioxide in the leaktight tank which would have been reached if the reaction had been complete.

Pth is calculated by the electronic calculating unit by application of the following formula:

$$Pth = Nth.R.T/V$$

in which:

Pth is expressed in pascals,

Nth is the theoretical number of moles of carbon dioxide which would have been produced if the reaction had been complete, R is the ideal gas constant, equal to 8.32 J. $K^{-1}$ .$mol^{-1}$, V represents the volume of the tank, expressed in cubic meters, T represents the temperature of the thermostatically-controlled bath, expressed in kelvins.

The values of Pth, Nth, V, T and R are calculated beforehand and introduced manually into the memory of the electronic calculating unit by means for the numeric keypad.

Nth is calculated from the BN (Basic Number) of the lubricant, determined beforehand according to the method described in ASTM Standard D 2896, from the mass of the lubricant introduced into the tank in order to form the film and from the acid used. BN is expressed as mg of potassium hydroxide per gram of lubricant.

The reaction rate, which is equal to the maximum rate of variation in the recorded pressure.

The values of the three parameters thus calculated are displayed on the liquid-crystal screen 26.

What is claimed is:

1. A method for estimating the neutralization capacity of a lubricant comprising basic detergent additives of known basicity consisting in reacting, in a leaktight tank (1), at a constant temperature, the bases contributed by the additives present in a sample of known mass of lubricant with a predetermined amount of a liquid acid determined from the Basic Number of lubricant calculated according to ASTM Standard D 2896, the method additionally consisting of:

forming, within the leaktight tank (1), a film from the lubricant sample, depositing the predetermined amount of liquid acid at the surface of the film in a time less than 0.5 second to initiate a neutralization reaction between the liquid acid and the bases in the lubricant, measuring the values of pressure of carbon dioxide formed in said reaction within the leaktight tank (1), recording the values of said pressure within the leaktight tank (1) as a function of time until said pressure has stabilized;

determining, from the recorded values of said pressure, at least one of the following three parameters defining the neutralization capacity of the lubricant: an initiation period for the neutralization reaction, a neutralization potential of the lubricant and a reaction rate of the neutralization reaction.

2. The method according to claim 1, wherein the initiation period for the neutralization reaction is determined by measuring the time elapsing between the moment when deposition of liquid acid starts and the moment when recorded pressure passes through a minimum value.

3. The method according to claim 1, wherein the neutralization potential is determined by application of the following formula:

$$Ra = \Delta P/Pth \times 100$$

in which:

Ra represents the neutralization potential in %, $\Delta P$ represents the difference between the stabilized recorded pressure value and the minimum value of the recorded pressure, Pth represents the theoretical pressure in the leaktight tank (1) which would have been reached if the reaction had been complete; Pth is calculated by application of the following formula:

$$Pth = Nth.R.T/V$$

in which,

Pth is expressed in pascals;

R is the ideal gas constant;

V represents the volume of the tank;

T represents the temperature of the thermostatically-controlled barth, and

Nth is the theoretical number of moles of carbon dioxide which would have been produced if the reaction had been complete, wherein Nth is calculated from the Basic Number of lubricant determined according to ASTM Standard D 2896 expressed in mg KOH/g of lubricant and Nth=(BN×masses of lubricant)/(2×KOH molar mass).

4. The method according to claim 1, wherein the reaction rate of the neutralization reaction is equal to the maximum rate of increase in the recorded pressure.

5. The method according to one of claims 1 to 4, wherein the lubricant film formed within the leaktight tank exhibits a thickness of between 20 and 150 microns.

6. The method according to one of claims 1 to 4, wherein the liquid acid is 95% sulfuric acid.

7. The method according to claim 6, wherein the predetermined amount of 95% sulfuric acid corresponds to an excess of acid of between 0.5% and 200% with respect to the amount of bases contributed by the detergent additives.

8. A device for estimating the neutralization capacity of a lubricant comprising detergent additives of known basicity, a leaktight tank (1) equipped with means for maintaining a constant temperature in which the bases contributed by the additives present in a sample of known mass of lubricant are reacted with a predetermined amount of a liquid acid at least equal to the stoichiometric amount, the device additionally comprising:

means (13, 14) for forming a film on an inner wall of the leaktight tank (1) from the lubricant sample, means (15) for depositing the predetermined amount of liquid acid at the surface of the film in a time less than 0.5 second, a pressure sensor (8) within the leaktight tank (1) delivering a pressure measurement signal to an output (9), a recording unit (19) connected to the output (9) of the pressure sensor (8), for recording values of the pressure within the leaktight tank as a function of time.

means (22) for determining at least one of the following three parameters defining the neutralization capacity of the lubricant: an initiation period for the neutralization reaction, a neutralization potential of the lubricant or a reaction rate of the neutralization reaction.

9. The device according to claim 8, wherein the means for determining the parameters defining the neutralization capacity of the lubricant consist of a unit for displaying a plot of recorded pressure against time values of recorded pressure as a function of time in a graduated-axis system, the said unit being connected to an output of the recording unit.

10. The device according to claim 9, wherein the initiation period for the neutralization reaction is determined from a plot of recorded pressure against time, by measuring the time elapsing between the moment when deposition of liquid acid starts and the moment when recorded pressure passes through a minimum value.

11. The device according to claim 9, wherein the neutralization potential is determined by application of the following formula:

$$Ra = \Delta P/Pth \times 100$$

in which:

Ra represents the neutralization potential in %, $\Delta P$ represents the difference between the stabilized recorded pressure value and the minimum value of the recorded pressure, Pth represents the theoretical pressure in the leaktight tank (1) which would have been reached if the neutralization reaction had been complete;

ΔP is determined from the plot of recorded pressure against time.

12. The device according to claim 9, wherein the reaction rate, equal to the maximum rate of increase in the recorded pressure, is determined from the plot of the recorded pressure against time.

13. The device according to claim 8, wherein it additionally comprises which delivers a signal for the beginning of deposition of liquid acid to an output connected to the recording unit and the means for determining the parameters defining the neutralization capacity of the lubricant consist of an electronic unit for calculating said parameters connected to an output of the recording unit.

14. The device according to claim 13, wherein the electronic calculating unit calculates the initiation period for the neutralization reaction, from the value of the recorded pressure and the signal delivered by said indicator for the deposition of liquid acid by calculating the time elapsing between the moment when deposition of liquid acid starts and the moment when the instant recorded pressure passes through a minimum value.

15. The device according to claim 13, wherein the electronic calculating unit calculates the neutralization potential of the lubricant by application of the following formula:

$$Ra = \Delta P / Pth \times 100$$

in which:

Ra represents the neutralization potential in %,

ΔP represents the difference between the stabilized recorded pressure value and the minimum value of the recorded pressure, Pth represents the theoretical pressure in the leaktight tank (1) which would have been reached if the neutralization reaction had been complete;

ΔP is calculated by the electronic calculating unit determined from the values of the recorded pressure.

16. The device according to claim 13, wherein the electronic calculating unit calculates the neutralization reaction rate from the values of the recorded pressure by calculating the maximum rate of increase in the recorded pressure.

17. The device according to claim 8, wherein said means for forming a film from the lubricant sample comprises magnetic bars and said means for depositing the predetermined amount of liquid acid comprises a syringe and needle.

18. The method according to claim 5 wherein the liquid acid is 95% sulfuric acid.

* * * * *